(12) United States Patent
Hörnberg

(10) Patent No.: US 6,171,271 B1
(45) Date of Patent: Jan. 9, 2001

(54) PRESSURE BANDAGE

(75) Inventor: Irene Hörnberg, Göteborg (SE)

(73) Assignee: Irene Hornberg, Gothenburg (SE)

(*) Notice: Under 35 U.S.C. 154(b), the term of this patent shall be extended for 0 days.

(21) Appl. No.: 09/214,402

(22) PCT Filed: Jun. 26, 1997

(86) PCT No.: PCT/SE97/01144
  § 371 Date: Dec. 23, 1998
  § 102(e) Date: Dec. 23, 1998

(87) PCT Pub. No.: WO97/49360
  PCT Pub. Date: Dec. 31, 1997

(51) Int. Cl.⁷ .................................................. A61F 5/00
(52) U.S. Cl. .................................. 602/13; 128/DIG. 20; 602/19
(58) Field of Search .............................. 602/5, 6, 13, 19; 128/DIG. 20

(56) References Cited

U.S. PATENT DOCUMENTS

| 2,823,668 | 2/1958 | Van . |
| 4,135,503 | 1/1979 | Romano . |
| 4,178,923 | 12/1979 | Curlee . |
| 4,270,527 | 6/1981 | Peters et al. . |

Primary Examiner—Michael A. Brown
(74) Attorney, Agent, or Firm—Orum & Roth

(57) ABSTRACT

The invention relates to a pressure bandage for hip joint prosthesis operated patients and including a portion which may be enclosed around the hips of said patient. The enclosing member is formed by a cloth-shaped inelastic girdle which exhibits Velcro® closing means at their connectable end parts, turned away from each other and towards each other. A pressure bladder to which means are connected for pressure control and fluid level filling, respectively, may be received inside said enclosing and connected girdle, wherein filling and emptying, respectively, of said pressure bladder enables producing the desired pressure upon the operated hip.

9 Claims, 4 Drawing Sheets

Figure 3:
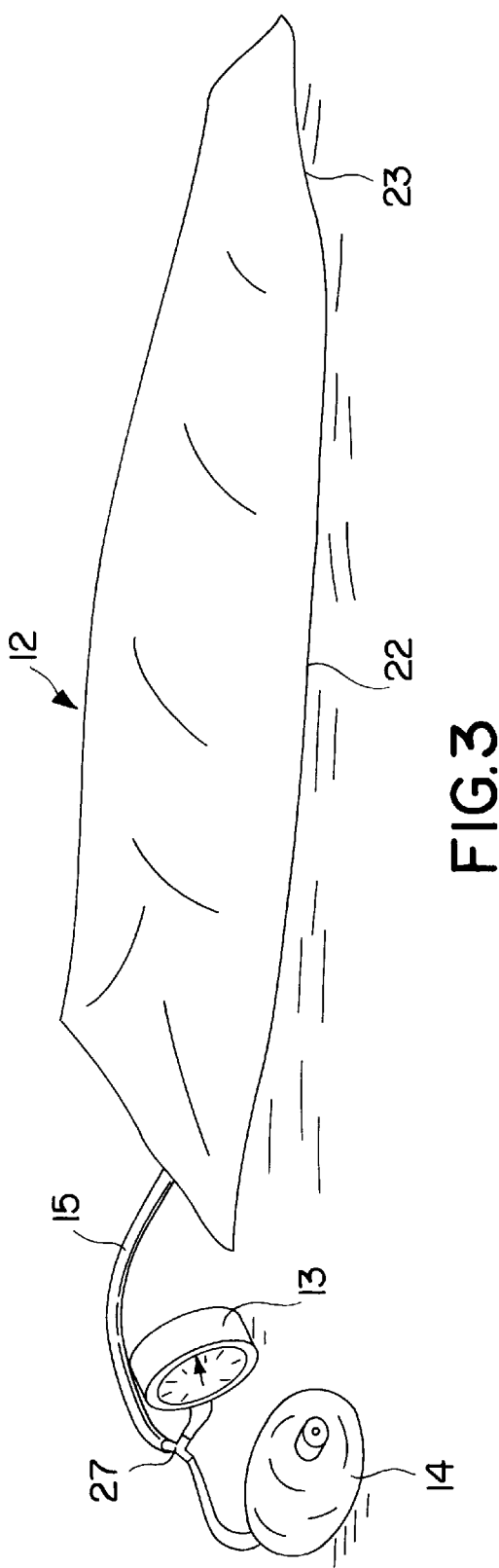

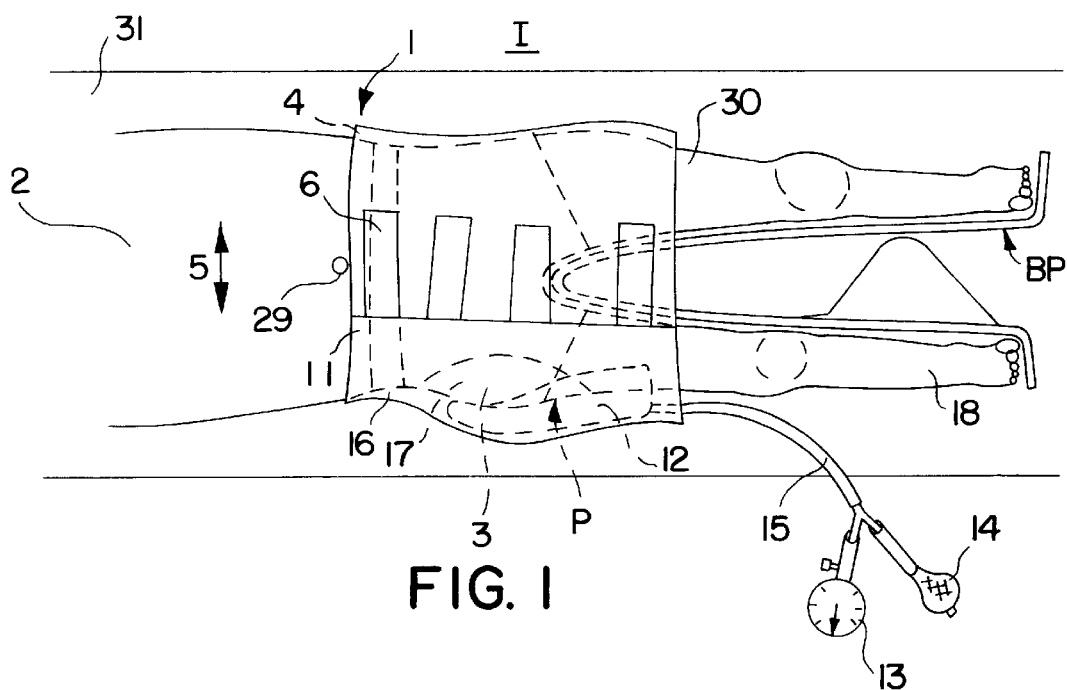
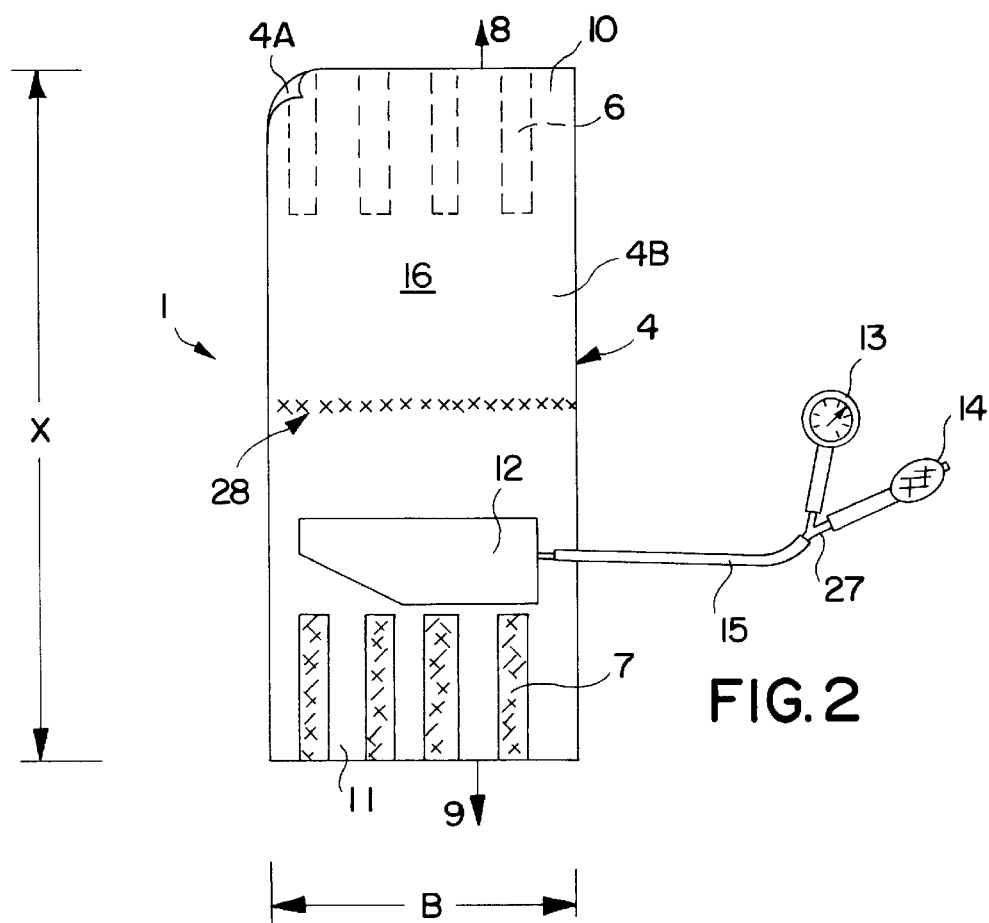

PRESSURE BANDAGE

The present invention concerns a pressure bandage for hip joint prosthesis operated patients and includes a portion which may be enclosed around the hips of said patient.

At prior art pressure bandages of the above mentioned type, it is difficult to inspect inside the bandage and in doing so opening and applying a new bandage again. In the course of a doctor binding up elastic bandages around the hip of the patient in the manner of a skirt/girdle with the appropriate pressure, at the same time six nurses must lift the patient straight up from a bed, which lead to an uncomfortable and detrimental operating position for the nurses, and that valuable time for the doctor is consumed for such tasks. Furthermore, the staff risk getting into contact with the blood of the patient. The pressure which is provided is then not controllable, which might be the cause of bedsore on sensitive patients. It may also be positioned too loosely and will then not have the desired effect, and large haematoma may arise, which may lead to serious consequences, for example infections and unnecessary loss of blood. This may also involve a longer process of healing and pain for the patient. During inspection, the bandages must be removed by cutting off and then they are thrown away in order to if necessary be replaced by new bandages, which leads to high bandage costs.

Through U.S. Pat. No. 4,270,527 is previously known a bandage trouser which is provided with inflatable bladders inside a trouser forming panel. This bandage trouser is in the first place intended for use as an aid of assistance when taking care of injured persons involved in an accident, like e.g. a vehicle accident. It is then important to be able to safely hold injured limbs in place during transport. There is for this object for instance an inflatable pressure bladder which is arranged inside in one of the legs of the bandage trouser. An additionally arranged pressure bladder is arranged inside the bandage trouser in the area around the waist of a patient.

Any effective supporting function for the hip of the patient longitudinally which is needed after a hip operation, is not enabled with the prior art bandage trouser. The fact is that it is very important and crucial with the shape of the supporting means during hip operations in order to get the right pressure to the operated area at the hip joint in order to avoid bleeding but still exert pressure onto the operation area.

The main object of the present invention is therefore in the first case to provide a pressure bandage which solves for instance the above mentioned problems and which also provides a multitude of additional advantages.

The object is achieved by means of a pressure bandage according to the present invention, which is principally characterized in that the enclosing portion is formed by a cloth-shaped inelastic girdle which exhibits Velcro closing means at their away from each other turned with each other—connectable end parts, that a pressure bladder which has an oblong shape tapering in the direction towards one of its short ends, substantially corresponding to the thickness of the patients hip and thigh, as seen when the patient lies on his back and to which means are connected for pressure control and fluid level filling respectively, may be received inside said enclosing and connected girdle, wherein filling and emptying respectively of said pressure bladder enables producing the desired pressure upon the operated hip.

The pressure bandage according to the present invention may be used as a preventive measure, and be used as pressure on tissue during bleeding in progress.

Advantages:
Controlled pressure,
facilitated inspection,
requiring less staff,
reduced risk for staff to come into contact with blood,
reduced cost for bandages,
fewer blood transfusions,
shorter process of healing.

Figure 4:
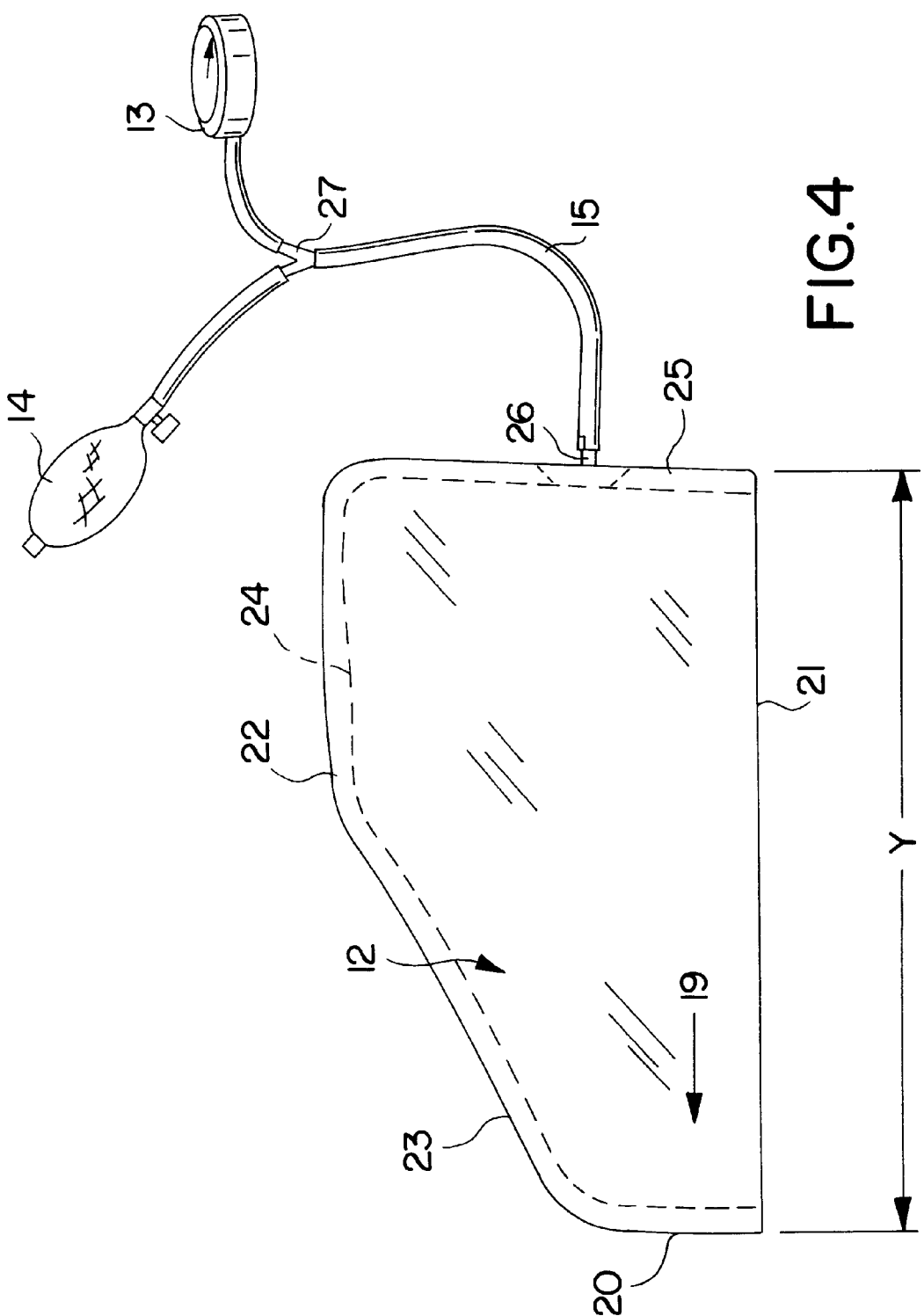
Figure 5:
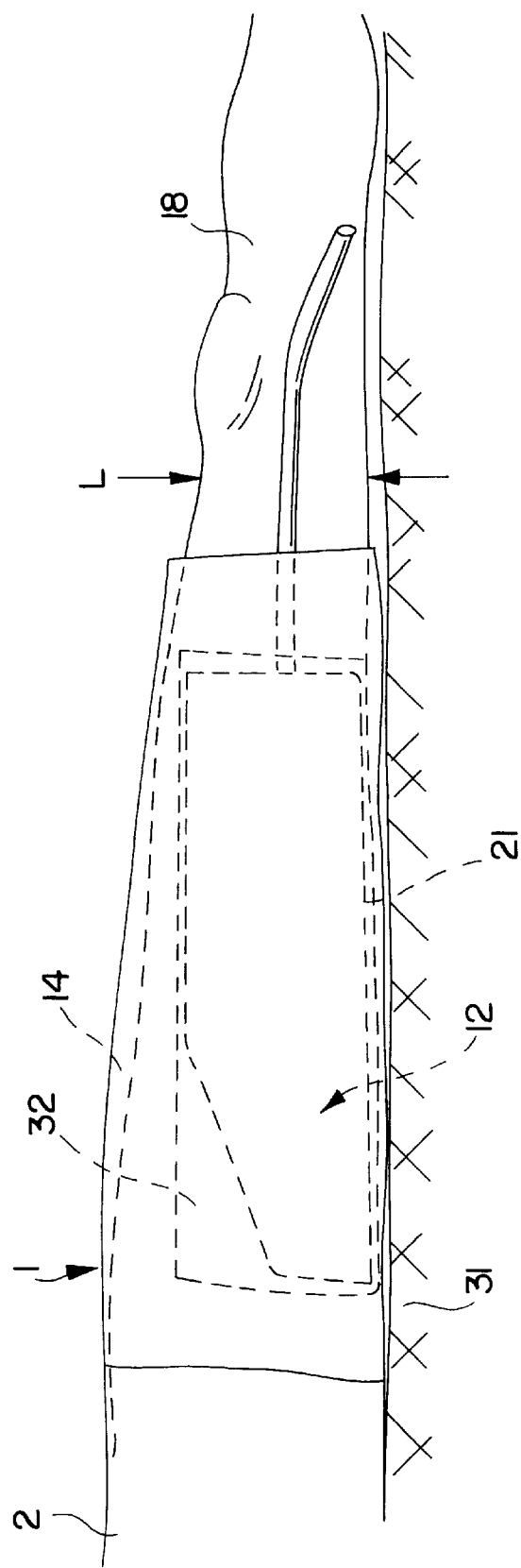

The invention will now be described here below as a preferred embodiment, by reference to the accompanying drawings in which:

FIG. 1 shows a schematic plan view of a patient which is equipped with a hip pressure bandage in operative position, FIG. 2 shows a plan view of the pressure bandage in widespread position ready for applying, FIG. 3 shows a perspective view of a pressure bladder which is a part of the pressure bandage, FIG. 4 shows the pressure bladder in widespread position seen from above and with illustrated appurtenant means for pressure control and for fluid level filling respectively, and FIG. 5 shows the pressure bandage in a side view in applied position.

A pressure bandage 1 according to the present invention which is intended to be used by a hip prosthesis operated patient 2 and including an around the hips 3 of said patient enclosing member 4, has said hip enclosing member formed by a cloth formed girdle. Said girdle 4, which is inelastic in the direction 5 around a patient 2 and which may be produced by a textile like for example BEAVERNYLON® with the shiny side turned outward, exhibiting preferably band shaped Velcro closing means 6, 7 on the girdle 4 at their away from each other 8, 9 turned with each other connectable end parts 10, 11. With inelastic should be understood that the girdle 4 should not be substantially compliant when subjected to force, but should form a support when a pressure is exercised on the girdle 4 towards its surface. A pressure bladder 12, which e.g. is formed of Neoprene, Latex or other gas-tight material, is also included in said pressure bandage 1 and to which means 13, 14 for pressure control and fluid level filling respectively are connected via a number of tubes 15. This pressure bladder 12 is in active bandaging position I, as is shown in FIG. 1, may be received inside 16 said enclosing and connected girdle 4. The filling and emptying respectively of said pressure bladder 12 then make possible to achieve the desirable pressure P against the operation spot 17 at the operated hip 3.

The pressure bladder 12 exhibits an oblong shape, substantially corresponding to the hip and thigh thickness L of the patient 2, as seen when the patient 2 lies on the back.

In order to get the correct pressure for the pressure bandage 1, i.e. not obstructing the arterial circulation in the leg 18 and that the pressure do not seem to be wrong in the groin of the patient 2, is the pressure bladder 12 designed so that it tapers in the direction 19 towards one of its short ends 20.

Preferably, the pressure bladder 12 exhibits a rectangular shape with a straight long side 21 and an opposite long side 22 which is provided with an edge member 23 which is inclined towards said one short end 20. Thereby excellent pressure conditions are obtained when applying the pressure bladder 12 in the bandage 1. The edges 24 of the bladder 12 may be formed by folded over and glued flaps along a number of circumference edges 20, 21, 22, 23, 25.

A connection 26 for pressure control and for fluid level filling respectively, start from the short end 25 which is opposed the tapering short end 20 of the pressure bladder, i.e. the longest short end 25.

A tube 15 with a y-connection 27 forms connection for a pressure gauge 13 and a pressure bladder 14 respectively.

The said girdle 4 is formed by a textile cloth with a substantially rectangular shape with the Velcro closing means 6, 7 attached to the respective side surface 4A 4B of the girdle 4, in the shape of longitudinal bands.

In order to facilitate exact positioning of the girdle 4 on the patient, a centre mark 28, for example in the form of a seam, may be arranged to extend on the girdle 4 across the longitudinal axis of the girdle. Furthermore, the width B of the girdle 4 is so chosen, that it covers approximately from the navel 29 of the patient 2 down to the thigh 30 of the patient. The girdle 4 may not press higher up the abdomen in order Lo avoid obstruction of respiration. The girdle 4 exhibits a length X which exceeds the waist-measurement of the patient in wrapped up position. The length Y of the bladder 12 fall short of the width B of the girdle. The function of the pressure bandage 1 has been described above and now the application of said bandage shall be described in brief:

The girdle 4 is positioned together with a leg plough BP in advance on to a bed 31 where the patient 2 will be resting, or is pushed in under an already resting patient 2 with preferably its smooth side 4A turned away from the patient 2 when it rests on the back. Then the pressure bladder 12 is positioned adjacent the hip 3 of the patient with its longest short side 21 turned down towards the sleeping pad 31. The pressure bandage 1 may thereby not be positioned so that it obstructs the arterial circulation inside the leg, i.e. it must not be positioned in the groin of the patient and not be inside the centre line of the thigh. Then the girdle 4 is folded around the patient 2 and is closed by means of the Velcro closing means 6, 7. Then the pressure bladder 12 is pumped up to the appropriate pressure, for example 20–30 mm Hg, or is adapted to the pain threshold of the patient.

A correct positioning of the pressure bladder 12 is then necessary in order to achieve the best result.

The girdle 4 also makes it simple to open the bandage 1 e.g. for enabling inspection of the operation spot and skin—the peripheral circulation of the hip and also around the torso when necessary.

In order to increase hygiene, a cover 32 may be used around the pressure bladder 12, e.g. a plastic pillowcase or else.

The bandage 1 may be recycled and may be cleaned in a dishwasher or a washing machine and may be dried after that.

The invention is not limited to the above described and in the drawings shown embodiment but may be varied within the scope of the accompanying claims without departing from the inventive concept.

I claim:

1. A pressure bandage for hip-joint prosthesis operated patients and including a portion which may be enclosed around the hips of said patients, wherein the enclosing portion is formed by a girdle which exhibits hook and loop or hook and pile closing means at their away from each other turned with each other connectable end parts, a pressure bladder which has an oblong shape tapering in the direction towards one of its short ends, substantially corresponding to the thickness of the patient's hip and thigh, as seen when the patient lies on his back, and to which are connected a "Y" shaped connecting tube connecting a pressure bladder for pressure control and fluid level filling, which may be received inside said inclosing and connected girdle, the "Y" shape connection tube being disposed at the short end adjacent the tapered shape of the pressure bladder, wherein filling and emptying respectively of said pressure bladder enables producing the desired pressure upon the operated hip.

2. A pressure bandage according to claim 1, wherein the pressure bladder (12) consist of a gas-tight material, especially Neoprene or Latex.

3. A pressure bandage according to claim 2, wherein the girdle is formed by a textile cloth with a substantially rectangular shape with a hook and loop or hook and pile closing means attached to a respective side surface of the girdle, in the shape of longitudinal bands and connected girdle, wherein filling and emptying respectively of said pressure bladder enables producing the desired pressure upon the operated hip.

4. A pressure bandage according to claim 1, wherein the girdle (4) is formed by a textile cloth with a substantially rectangular shape with the hook and loop or hook and pile closing means (5, 6) attached to a respective side surface (4A, 4B) of the girdle, in the shape of longitudinal bands.

5. A pressure bandage according to claim 4, wherein a centre mark (28) extending across the longitudinal axis of the girdle is arranged on the girdle (4).

6. A pressure bandage according to claim 5, wherein the width (B) of the girdle (4) is so chosen, that it covers from the level of the navel (29) down to the thigh (30) of the patient and exhibiting a length (X) which exceeds the waist-measurement of the patient.

7. A pressure bandage according to claim 1, wherein the girdle is formed by a textile cloth with a substantially rectangular shape with a hook and loop or hook and pile closing means attached to a respective side surface of the girdle, in the shape of longitudinal bands.

8. A pressure bandage according to claim 1 wherein a connection for pressure control and fluid level filling respectively start from that short end which is directed towards the tapering short end of the pressure bladder.

9. A pressure bandage for hip-joint prosthesis operated patients and including a portion which may be enclosed around the hips of said patients, wherein the enclosing portion is formed by a girdle which exhibits hook and loop or hook and pile closing means at their away from each other turned with each other connectable end parts, a pressure bladder which has an oblong shape tapering in the direction towards one of its short ends, the pressure bladder further having a rectangular type shape with a straight long side and an opposite long side and which is provided with a portion inclined towards the short end, substantially corresponding to the thickness of the patient's hip and thigh, as seen when the patient lies on his back, and to which a "Y" shaped connecting tube connecting a pressure gauge with bladder for pressure control and fluid level filling, which may be received inside said enclosing and connecting girdle, wherein filling and emptying respectively of said pressure bladder enables producing the desired pressure upon the operated hip.

* * * * *